US011089982B2

(12) United States Patent
Perea et al.

(10) Patent No.: US 11,089,982 B2
(45) Date of Patent: *Aug. 17, 2021

(54) ROBUST FRACTIONAL SATURATION DETERMINATION

(71) Applicant: MASIMO CORPORATION, Irvine, CA (US)

(72) Inventors: Philip Perea, Irvine, CA (US); Ammar Al-Ali, San Juan Capistrano, CA (US); Massi Joe E. Kiani, Laguna Niguel, CA (US)

(73) Assignee: MASIMO CORPORATION, Irvine, CA (US)

( * ) Notice: Subject to any disclaimer, the term of this patent is extended or adjusted under 35 U.S.C. 154(b) by 110 days.

This patent is subject to a terminal disclaimer.

(21) Appl. No.: 16/387,352

(22) Filed: Apr. 17, 2019

(65) Prior Publication Data
US 2019/0307377 A1 Oct. 10, 2019

Related U.S. Application Data

(63) Continuation of application No. 15/795,007, filed on Oct. 26, 2017, now Pat. No. 10,299,709, which is a continuation of application No. 13/791,633, filed on Mar. 8, 2013, now Pat. No. 9,808,188, which is a continuation-in-part of application No. 13/650,730, filed on Oct. 12, 2012, now abandoned.

(60) Provisional application No. 61/703,688, filed on Sep. 20, 2012, provisional application No. 61/547,001, filed on Oct. 13, 2011.

(51) Int. Cl.
*A61B 5/1455* (2006.01)
*A61B 5/00* (2006.01)

(52) U.S. Cl.
CPC ........ *A61B 5/14551* (2013.01); *A61B 5/7203* (2013.01); *A61B 5/7221* (2013.01)

(58) Field of Classification Search
CPC .............. A61B 5/1455; A61B 5/14551; A61B 5/14553; A61B 5/0059; A61B 5/0075; A61B 5/72; A61B 5/7271
See application file for complete search history.

(56) References Cited

U.S. PATENT DOCUMENTS

| | | | |
|---|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |

(Continued)

OTHER PUBLICATIONS

US 8,845,543 B2, 09/2014, Diab et al. (withdrawn)

Primary Examiner — Eric F Winakur
(74) Attorney, Agent, or Firm — Knobbe, Martens, Olson & Bear, LLP

(57) ABSTRACT

The present disclosure describes the derivation and measurement of a fractional oxygen saturation measurement. In one embodiment, a system includes an optical sensor and a processor. The optical sensor can emit light of multiple wavelengths directed at a measurement site of tissue of a patient, detect the light after attenuation by the tissue, and produce a signal representative of the detected light after attenuation. The processor can receive the signal representative of the detected light after attenuation and determine, using the signal, a fractional oxygen saturation measurement based on two or more different measures of fractional oxygen saturation.

19 Claims, 7 Drawing Sheets

(56) References Cited

U.S. PATENT DOCUMENTS

| | | |
|---|---|---|
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,842,979 A | 12/1998 | Jarman |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,983,122 A | 11/1999 | Jarman |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,104,938 A | 8/2000 | Huiku et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |

(56) References Cited

U.S. PATENT DOCUMENTS

| | | | |
|---|---|---|---|
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |

(56) References Cited

U.S. PATENT DOCUMENTS

| | | |
|---|---|---|
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |

(56) References Cited

U.S. PATENT DOCUMENTS

| | | |
|---|---|---|
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |

(56) References Cited

U.S. PATENT DOCUMENTS

| | | |
|---|---|---|
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0111748 A1 | 8/2002 | Kobayashi et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0261979 A1 | 10/2010 | Kiani |
| 2010/0270257 A1 | 10/2010 | Wachman et al. |
| 2011/0001605 A1 | 1/2011 | Kiani et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0123231 A1 | 5/2012 | O'Reilly |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0045685 A1 | 2/2013 | Kiani |
| 2013/0046204 A1 | 2/2013 | Lamego et al. |
| 2013/0041591 A1 | 3/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2013/0345921 A1 | 12/2013 | Al-Ali et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |

(56) References Cited

U.S. PATENT DOCUMENTS

| | | |
|---|---|---|
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0005600 A1 | 1/2015 | Blank et al. |
| 2015/0011907 A1 | 1/2015 | Purdon et al. |
| 2015/0018650 A1 | 1/2015 | Al-Ali et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2016/0196388 A1 | 7/2016 | Lamego |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |

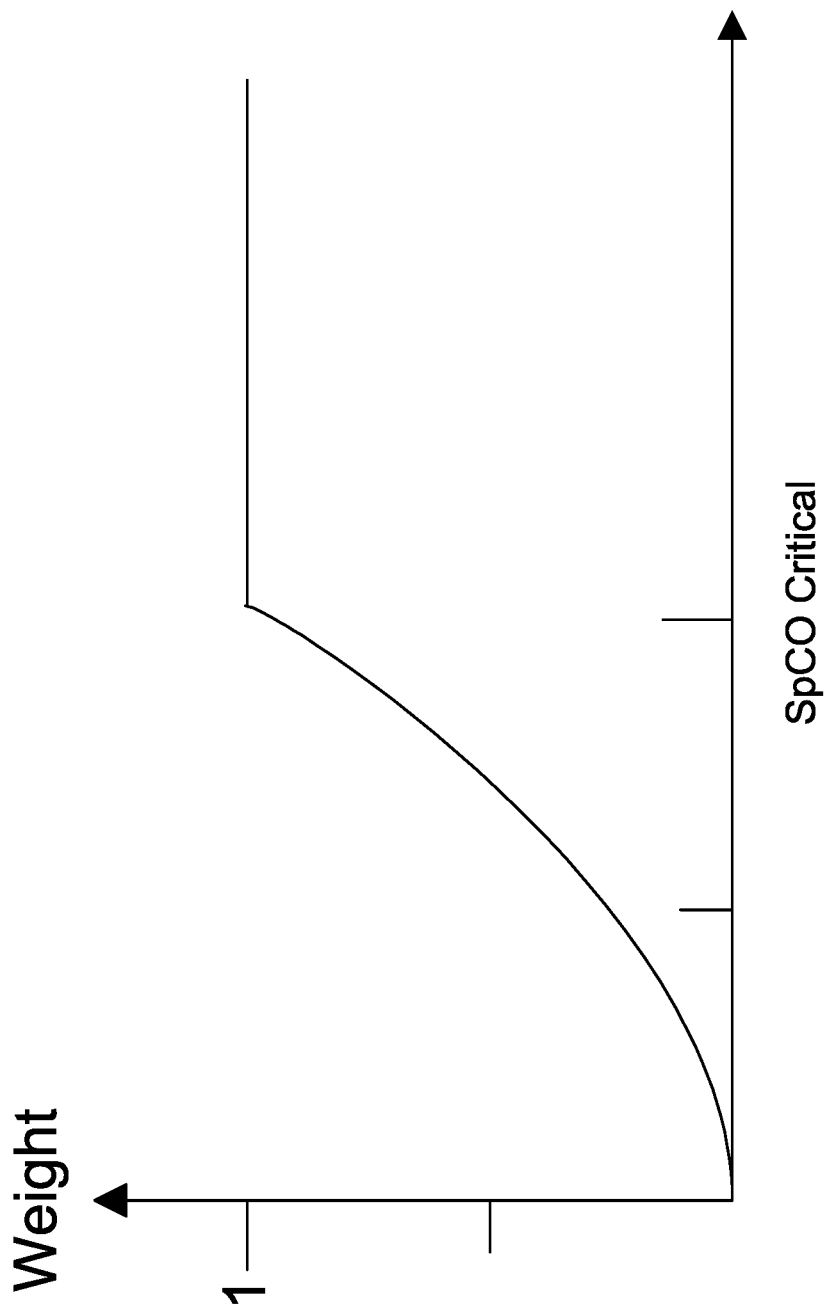

ROBUST FRACTIONAL SATURATION DETERMINATION

PRIORITY CLAIM TO RELATED APPLICATIONS

The present application is a continuation of U.S. patent application Ser. No. 15/795,007, filed Oct. 26, 2017, entitled "Robust Fractional Saturation Determination," which is a continuation of U.S. patent application Ser. No. 13/791,633, filed Mar. 8, 2013, entitled "Robust Fractional Saturation Determination," which is a continuation-in-part of U.S. patent application Ser. No. 13/650,730, filed Oct. 12, 2012, entitled "Robust Fractional Saturation Determination," which claims priority benefit under 35 U.S.C. § 119(e) of U.S. Provisional Application Ser. No. 61/703,688, filed Sep. 20, 2012, entitled "Robust Fractional Saturation Determination," and U.S. Provisional Application Ser. No. 61/547,001, filed Oct. 13, 2011, entitled "Robust Fractional Saturation Determination;" the disclosures of which are incorporated herein by reference.

FIELD OF THE DISCLOSURE

The present disclosure relates to the field of non-invasive optical based physiological measurements.

BACKGROUND

Pulse oximeters are well known and accepted for use in clinical environments. Pulse oximeters measure the relative percentage of oxygen carrying hemoglobin molecules in the blood. This measurement is commonly referred to as oxygen saturation or $SpO_2$. Pulse oximeters generally shine light of predetermined wavelengths at a measurement site on the patient and measure the attenuation of the light by the tissue using a detector. Some Pulse oximeters also include additional capabilities to measure other blood analyte levels in addition to oxygen saturation. Non-invasive measurement devices capable of measuring multiple physiological parameters, including oxygen saturation, methemoglobin levels and carboxyhemoglobin levels, are available from Masimo Corporation of Irvine Calif.

SUMMARY

Oxygen saturation provides a measure of the percentage of oxygenated hemoglobin to non-oxygenated hemoglobin. However, oxygen saturation does not take into account dishemoglobins including methemoglobin or carboxyhemoglobin that may affect the actual number of total hemoglobin molecules carrying oxygen. This is a serious problem when, for example, a patient with elevated dishemoglobins measures a high oxygen saturation measurement. Although the oxygen saturation measurement may be high, the patient may be in need of oxygen therapy because the patient's total capacity to carry oxygen is lowered by the effects of the dishemoglobins. Thus, despite a high oxygen saturation measurement, the patient may need additional oxygen.

Embodiments of the present disclosure provide a measurement of fractional oxygen saturation that takes into account dishemoglobins, such as, for example, carboxyhemoglobin and methemoglobin and provides a care giver with a more accurate picture of the patient's blood analyte.

BRIEF DESCRIPTION OF THE DRAWINGS

FIG. 3 illustrates a chart for weighting a carboxyhemoglobin measurement when methemoglobin is low.

DETAILED DESCRIPTION

Figure 1:
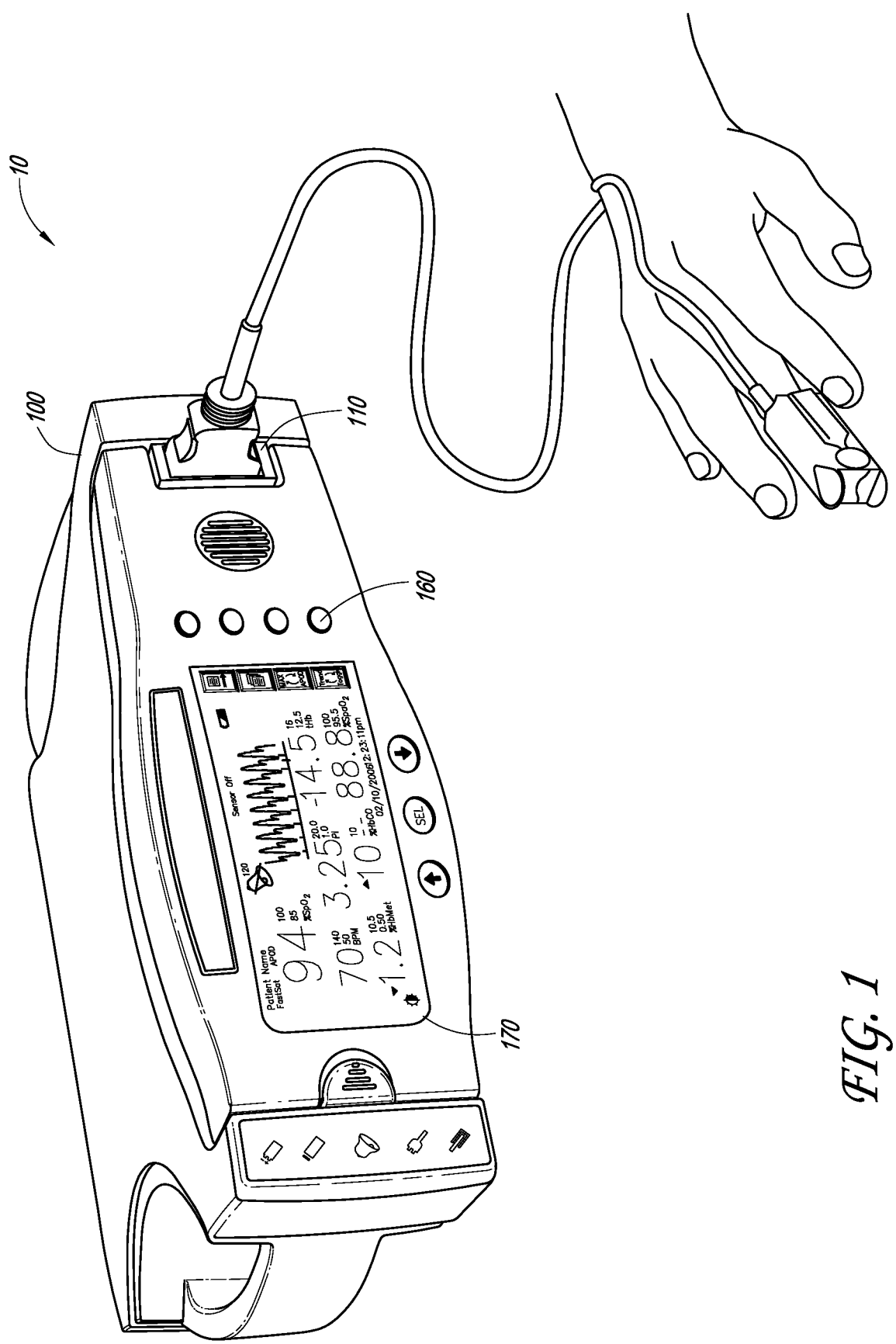
FIG. 1 illustrates an embodiment of a physiological measurement device according to an embodiment.

FIG. 1 illustrates an embodiment of a physiological measurement system 10 configured to determine a fractional oxygen saturation measurement. The system 10 includes a patient monitor 100 and optical sensor 200. The Monitor 100 includes a display screen 170, various user inputs 160 and sensor port 110. The sensor 200 includes emitters for emitting light of a plurality of wavelengths and a detector which detects light attenuated by tissue and generates a signal representative of the detected light. In operation, the patient monitor 100 sends drive signals to sensor 200 that turn the emitters on and off. The detector detects the light produced by the emitters after attenuation by the tissue. The detector generates a signal representative of the detected light and communicates the signal to the patient monitor 100. The patient monitor 100 includes a processor and other signal processing circuitry for processing the signal and determining physiological measurements from the signal. Greater detail of the patient measurement system 10 is disclosed in U.S. Pat. No. 7,764,982 entitled "Multiple Wavelength Sensor Emitters," the contents of which is expressly incorporated herein in its entirety.

Figure 2:
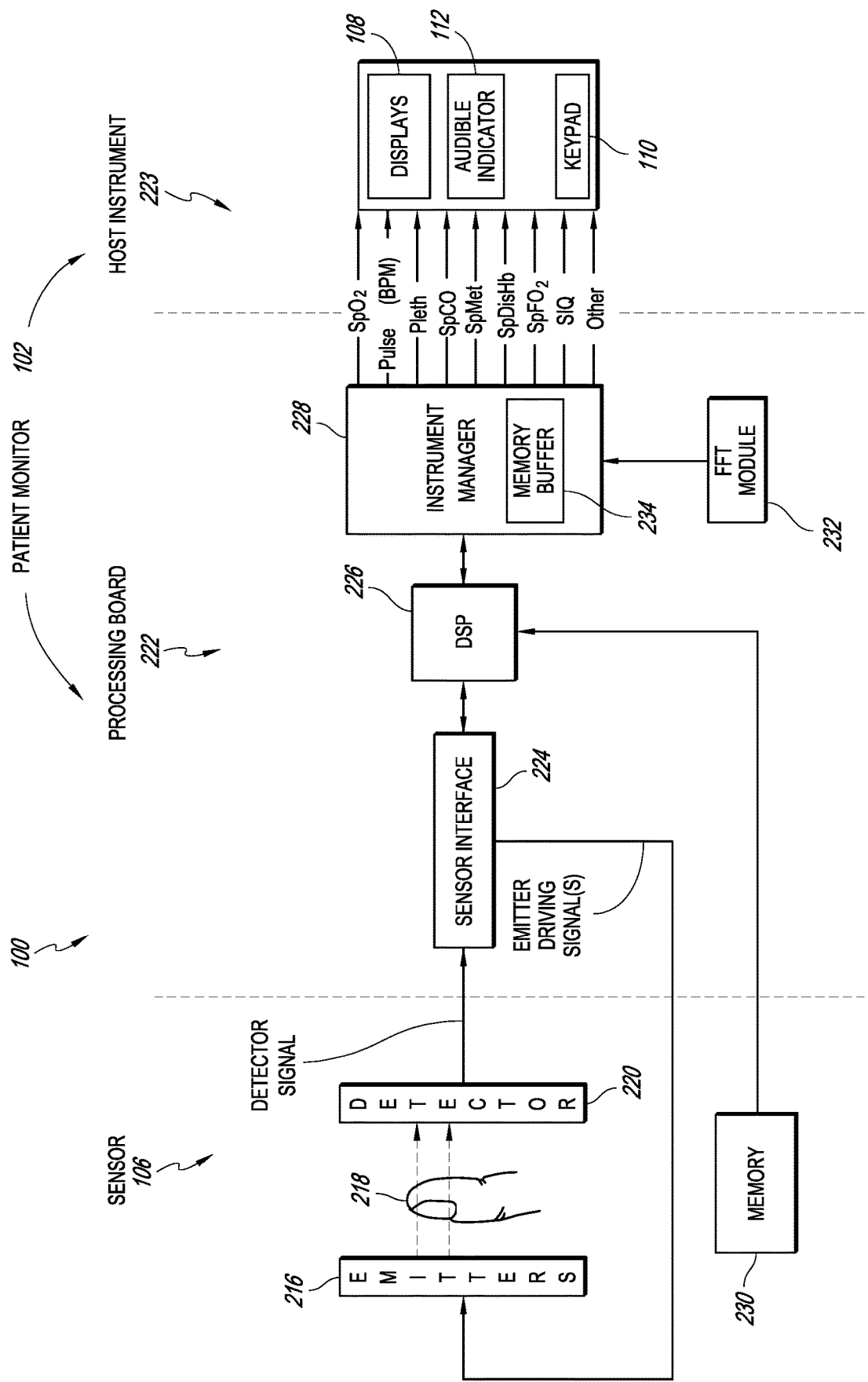
FIG. 2 illustrates a schematic diagram of an embodiment of a physiological measurement device according to an embodiment.

FIG. 2 illustrates details of an embodiment of a physiological measurement system 100 in a schematic form. Typically a sensor 106 includes energy emitters 216 located on one side of a patient monitoring site 218 and one or more detectors 220 located generally opposite. The patient monitoring site 218 is usually a patient's finger (as pictured), toe, ear lobe, or the like. Energy emitters 216, such as LEDs, emit particular wavelengths of energy through the flesh of a patient at the monitoring site 218, which attenuates the energy. The detector(s) 220 then detect the attenuated energy and send representative signals to the patient monitor 102. In an embodiment, 8 LEDs are used. In an embodiment 10 LEDs are used. In an embodiment, the LEDs have nominal wavelengths of about 620 nm, 630 nm, 650 nm, 660 nm, 730 nm, 805 nm, 905 nm, 1170 nm, 970 nm, 1270-1300 nm. Of course other nominal wavelengths in the same general range can be used as will be appreciated by a person of skill in the art.

In an embodiment, the patient monitor 102 includes processing board 222 and a host instrument 223. The processing board 222 includes a sensor interface 224, a digital signal processor (DSP) 226, and an instrument manager 228.

The host instrument typically includes one or more displays 108, control buttons 110, a speaker 112 for audio messages, and a wireless signal broadcaster. Control buttons 110 may comprise a keypad, a full keyboard, a track wheel, and the like. Additionally embodiments of a patient monitor 102 can include buttons, switches, toggles, check boxes, and the like implemented in software and actuated by a mouse, trackball, touch screen, or other input device.

The sensor interface 224 receives the signals from the sensor 106 detector(s) 220 and passes the signals to the DSP 226 for processing into representations of physiological parameters. These are then passed to the instrument manager 228, which may further process the parameters for display by the host instrument 223. In some embodiments, the DSP 226 also communicates with a memory 230 located on the sensor 106; such memory typically contains information related to the properties of the sensor that may be useful in processing the signals, such as, for example, emitter 216 energy wavelengths. The elements of processing board 222 provide processing of the sensor 106 signals. Tracking medical signals is difficult because the signals may include various anomalies that do not reflect an actual changing patient parameter. Strictly displaying raw signals or even translations of raw signals could lead to inaccurate readings or unwarranted alarm states. The processing board 222 processing generally helps to detect truly changing conditions from limited duration anomalies. The host instrument 223 then is able to display one or more physiological parameters according to instructions from the instrument manager 228, and caregivers can be more confident in the reliability of the readings. Among the various parameters that can be display are $SpO_2$ (Oxygen Saturation), SpMet (Methemoglobin), SpCO (Carboxyhemoglobin), a combined dishemoglobin measurement (referred to herein as SpDisHb), and directly measured or derived Fractional Oxygen Saturation, referred to herein as $SpFO_2$ or $SpFracO_2$ among other parameters including those illustrated in FIG. 2.

In an embodiment, a direct measurement of fractional oxygen saturation is obtained from the plethysmograph data using DSP 226. The measurement is based on empirically obtained data which is correlated with gold standard invasive measurements of fractional oxygen saturation which is used to obtain a calibration curve.

In another embodiment, a direct measurement of dishemoglobins are obtained. The dishemoglobin measurement is also obtained from the plethysmograph data using DSP 226. The measurement is based on empirically obtained data which is correlated with gold standard invasive measurements of dishemoglobins which is used to obtain a calibration curve. The dishemoglobin measurement is then used in conjunction with the oxygen saturation measurement as described below in order to obtain a fraction oxygen saturation measurement.

In yet another embodiment, a direct measurement of carboxyhemoglobin and methemoglobin is obtained and used to determine a fractional oxygen saturation measurement as described below.

In an embodiment, two or more of the above described processes for obtaining a fractional oxygen saturation measurement are used at the same time in order to obtain a more accurate measurement of oxygen saturation. For example, the various fractional oxygen saturation measurements can be compared or averaged. In an embodiment, signal confidence is determined for each measurement and used to determine which measurement determination is the best determination to use. In an embodiment, when signal confidence is low, the carboxyhemoglobin and methemoglobin measurements are used to determine a fraction saturation measurement. In an embodiment, when the signal confidence is high, a direct measurement of either the dishemoglobin or of the fraction oxygen saturation itself is used.

In an embodiment, the determination of fractional oxygen saturation begins with the understanding that hemoglobin in the blood falls into one of three categories. The three categories are: oxygenated hemoglobin, deoxygenated hemoglobin and dishemoglobins. Dishemoglobins include, for example, methemoglobin and carboxyhemoglobin. There may be additional categories of hemoglobin depending on patient conditions and inhaled toxins, however, for purposes of this fractional saturation measurement, it is assumed that these conditions are rare and/or negligible and are accounted for in the dishemoglobin measurement. Next, it is assumed that the relative fraction measured of these three categories of hemoglobin will add up to unity. This can be expressed mathematically as follows:

$$fRHb + fO_2Hb + fDisHb = 1 \qquad 1$$

where fRHb, $fO_2Hb$ and fDisHb represent the fraction of the total amount of available hemoglobin that is in each hemoglobin state, deoxygenated hemoblogin, oxygenated hemoglobin and dishemoglobins. In an embodiment, the dishemoglobin measurement can be mathematically represented as:

$$fDisHb = fMetHb + fCOHb \qquad 2$$

Typical pulse oximeters measure an oxygen saturation measurement that is referred to as a functional oxygen saturation measurement or SaO2. Functional oxygen saturation is the percentage of oxygenated blood compared to total potential oxygen carrying capacity of the combined oxygenated and deoxygenated hemoglobin species. Functional oxygen saturation can be mathematically represented as follows:

$$SaO2\,(\%) = \frac{fO_2Hb}{fRHb + fO_2Hb} * 100\% \qquad 3$$

True fractional oxygen saturation or $SpFO_2$, as defined herein, provides a measure of oxygenated hemoglobin compared to the total of all hemoglobin in the blood. This includes oxygenated hemoglobin and deoxygenated hemoglobin as well as dishemoglobins (including methemoglobin and carboxyhemoglobin, for example). In an embodiment, fraction oxygen saturation is measured directly from the plethysmograph. Fractional oxygen saturation can also be mathematically represented as follows:

$$SpFO2\,(\%) = \frac{fO_2Hb}{fRHb + fO_2Hb + fDisHb} * 100\% \qquad 4$$

Fractional oxygen saturation can be measured directly or derived from measureable parameters. As discussed above, typical pulse oximeters measure functional oxygen saturation. Some physiological measurement devices sold and marketed under the Rainbow® mark by Masimo Corp. of Irvine, Calif. are capable of measuring methemoglobin and carboxyhemoglobin in addition to functional oxygen saturation. Additionally, the dishemoglobins can be measured directly together as a single parameter combining methemoglobin and carboxyhemoglobin as well as other dishemoglobins in order to avoid anomalies introduced by separate measurements. As described below, fractional oxygen saturation can be determined using measurements of $SpO_2$, SpMet and SpCO. The following equations separate carboxyhemoglobin and methemoglobin measurements, however, it is to be understood that the carboxyhemoglobin and methemoglobin measurements need not be separate measurements but can be substituted for a single separate dishemoglobin measurement. Thus, for example, in equation 4 below, fMetHb+fCOHb can be substituted out for a single fDisHb (fractional dishemoglobin) measurement.

Equation 1 above can be mathematically rewritten as follows using a separate methemoglobin measurement and carboxyhemoglobin measurement instead of a single dishemoglobin measurement:

$$fRHb + fO_2Hb = 1 - fMetHb - fCOHb \qquad 4$$

Equation 3 above can also be mathematically rewritten as follows so that the left side of the equation matches the left side of equation 4:

$$fRHB + fO_2Hb = \frac{fO_2Hb}{SaO2} * 100\% \qquad 5$$

Equations 4 and 5 can be combined as follows:

$$\frac{fO_2Hb}{SaO2} * 100 = 1 - fMetHB - fCOHb \qquad 6$$

Equation 6 can then be mathematically rewritten as follows:

$$fO_2Hb = \frac{(1 - fMetHb - fCOHb) * SaO2}{100} \qquad 7$$

Equation 7 can be multiplied by 100 to express fO2Hb, fMetHb, and fCOHb as a percentage, leading to the final equation for fractional oxygen saturation:

$$O_2Hb = \frac{(100 - MetHb - COHb) * SaO2}{100} \qquad 8$$

Finally, rewriting Equation 8 in terms of measureable parameters using a Masimo Rainbow patient monitor provides the following equation:

$$SpFO_2 = \frac{(100 - SpMet - SpCO) * SpO2}{100} \qquad 9$$

Equation 9 above thus provides a calculated fractional saturation measurement that will give a patient care provider a more accurate indication of the physiological state of the patient.

One issue that arises with equation 9 is the accuracy of the various measurements involved. In particular, if one measurement is inaccurate, the accuracy of the fractional oxygen saturation measurement can be significantly affected. In order to minimize error in the fractional oxygen saturation measurement, the accuracy of the various measurements that form the fractional oxygen saturation measurement are determined. If one or more of the measurements are considered unreliable or inaccurate, weights or adjustments can be added in order to increase the reliability of the fractional oxygen saturation measurement.

In one embodiment, a rule based system is provided which analyzes the measurements based on various rules and adjusts parameter values in accordance with those rules. For example, if one parameter has a low confidence it can be down weighted in the determination of fractional oxygen saturation. Alternatively a confidence measure can be derived from the fractional oxygen measurement based on the confidence measure of SpO2, SpMet and SpCO. Many specific rules can be implanted to account for inaccuracies in the measurement.

In one embodiment, for example, high methemoglobin levels can impact the measurements of both carboxyhemoglobin and oxygen saturation. Thus, the present disclosure provides a rule based system for accounting for potential measurement inaccuracies during certain conditions.

In an embodiment, a more robust measurement of oxygen saturation is used. This measurement, referred to herein as Sp02_Robust, is determined using 2 or more wavelengths and a higher order polynomial fit. In an embodiment, 3 or more wavelengths can be used. In an embodiment, 5 wavelengths and a 3rd order polynomial equation are used to determine a more robust oxygen saturation measurement. Thus, equation 9 can be modified to:

$$SpFO_2 \ (\%) = \frac{(100 - SpMet - SpCO) * SpO2\_Robust}{100} \qquad 10$$

In an embodiment, a correction to SpCO is provided. As methemoglobin levels increase, the measurement of SpCO can be affected. In order to compensate for this, the following set of rules can be used. If the SpMet measurement is greater than a critical threshold, for example, about 2.2%, then the SpCO measurement is considered unreliable. This is referred to throughout this disclosure as a high methemoglobin condition. In this situation, SpCO is set to a relatively average SpCO measurement. In an embodiment, this can be the population average. In an embodiment, SpCO is set to about 0.9%.

In one embodiment, if the SpMet measurement is below the high methemoglobin measurement threshold, then the SpCO measurement is weighted. This is referred to throughout this disclosure as a low methemoglobin condition. In an embodiment, the weighting provided to the SpCO measurement is directly related to the SpCO measurement. By way of example, the weighting scale depicted in FIG. 3 illustrates an embodiment of a weighting scheme for SpCO values. As depicted in FIG. 3, the greater the SpCO measurement, the greater the weight provided. In an embodiment, the SpCO critical value is about 7% to about 8%. Other weighting schemes can also be used. For example, a purely linear, exponential, partially linear and partially non-linear weighting scales could be used as well. In an embodiment, the SpCO critical value can be higher or lower.

In one embodiment, if the SpMet measurement is less than a low methemoglobin measurement threshold, then the SpCO measurement is weighted as discussed above. In an embodiment, a low SpMet measurement is below about 1%. If the SpMet measurement is between a low methemoglobin value and a high methemoglobin value, then the measured parameters are used without adjustment.

Figure 4A:
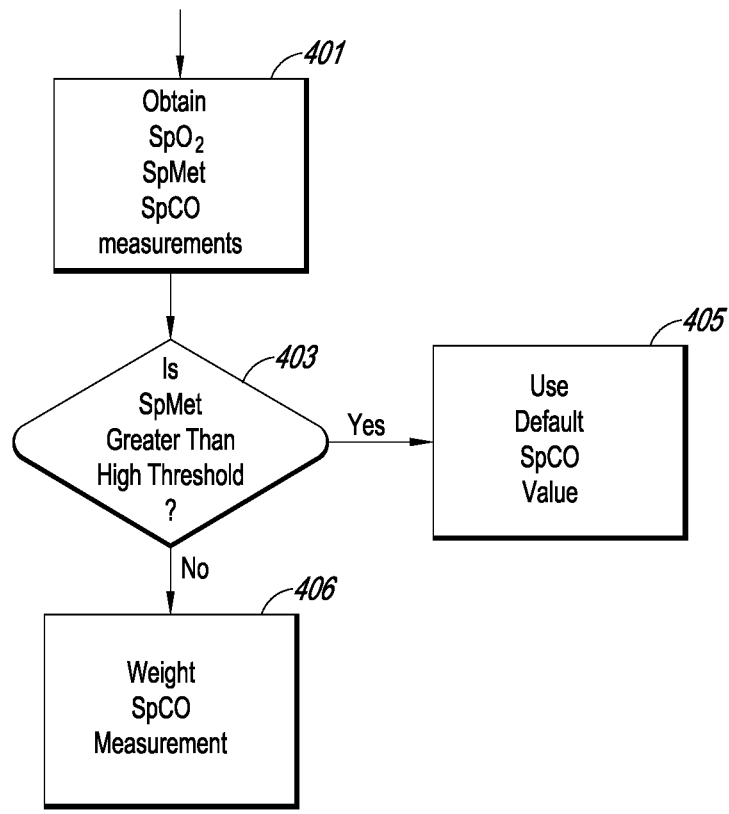
FIGS. 4A-C illustrate flowcharts detailing rules for determining carboxyhemoglobin measurements in view of methemoglobin measurements.

FIG. 4A illustrates an embodiment of a flow chart for determining whether a carboxyhemoglobin measurement needs to be adjusted. At step 401, oxygen saturation, carboxyhemoglobin and methemoglobin measurements are obtained. In an embodiment, the oxygen saturation measurement is a robust oxygen saturation measurement. The process moves to step 403 where a determination is made as to whether the methemoglobin measurement is greater than a threshold. If the answer is yes, the at step 405, a default carboxyhemoglobin measurement value is used. If, at step 403, the answer is no, the process moves to step 406 where the carboxyhemoglobin measurement value is weighted as described above.

Figure 4B:
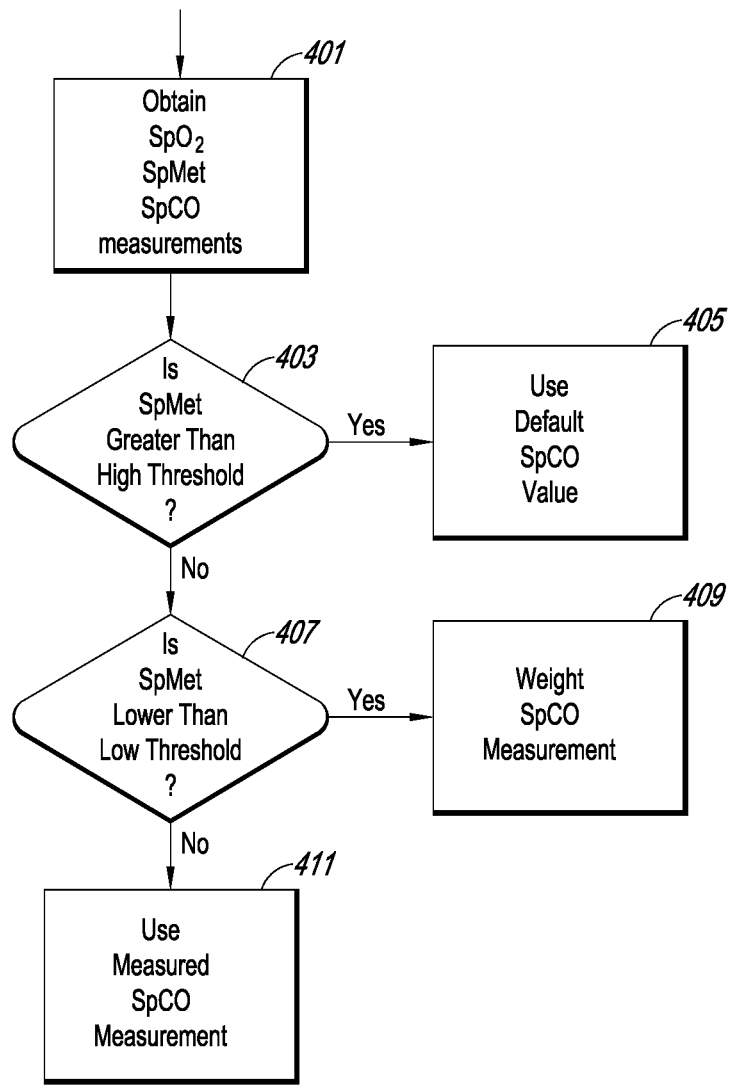

FIG. 4B illustrates another embodiment of a flow chart for determining whether a carboxyhemoglobin measurement needs to be adjusted. At step 401, oxygen saturation, carboxyhemoglobin and methemoglobin measurements are obtained. In an embodiment, the oxygen saturation measurement is a robust oxygen saturation measurement. The process moves to step 403 where a determination is made as to whether the methemoglobin measurement is greater than a threshold. If the answer is yes, the at step 405, a default carboxyhemoglobin measurement value is used. If, at step 403, the answer is no, the process moves to step 407. At step 407, the determination is made as to whether the methemoglobin measurement is lower than a low threshold. If the answer is yes, then the carboxyhemoglobin measurement value is weighted as described above. If the answer is no at step 407, the process moves onto step 411 where the measured carboxyhemoglobin value is used in the above described process for determining a fractional oxygen saturation.

Figure 4C:
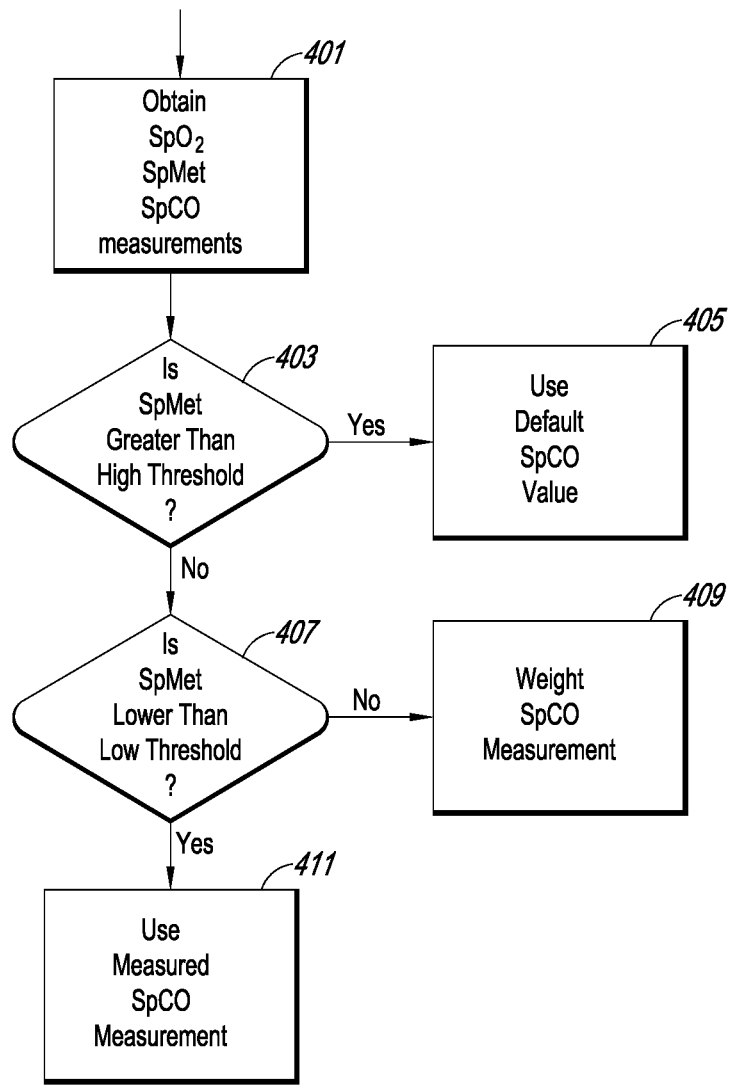

FIG. 4C illustrates another embodiment of a flow chart for determining whether a carboxyhemoglobin measurement needs to be adjusted. At step 401, oxygen saturation, carboxyhemoglobin and methemoglobin measurements are obtained. In an embodiment, the oxygen saturation measurement is a robust oxygen saturation measurement. The process moves to step 403 where a determination is made as to whether the methemoglobin measurement is greater than a threshold. If the answer is yes, the at step 405, a default carboxyhemoglobin measurement value is used. If, at step 403, the answer is no, the process moves to step 407. At step 407, the determination is made as to whether the methemoglobin measurement is lower than a low threshold. If the answer is no, then the carboxyhemoglobin measurement value is weighted as described above. If the answer is yes at step 407, the process moves onto step 411 where the measured carboxyhemoglobin value is used in the above described process for determining a fractional oxygen saturation.

In an embodiment, a multivariate classifier is used to determine whether the SpMet and SpCO values should be categorized as either a high or low methemoglobin condition. The multivariate classifier determines clusters of classifications based on empirically obtained measurement data. The measurement under analysis is then compared with the multivariate classification information in order to determine into which classification, or cluster, the measurement should be placed. Once the measurement under analysis is classified into either a high or low methemoglobin condition, then the actions described above with respect to the high and low methemoglobin conditions respectively are taken.

Figure 5:
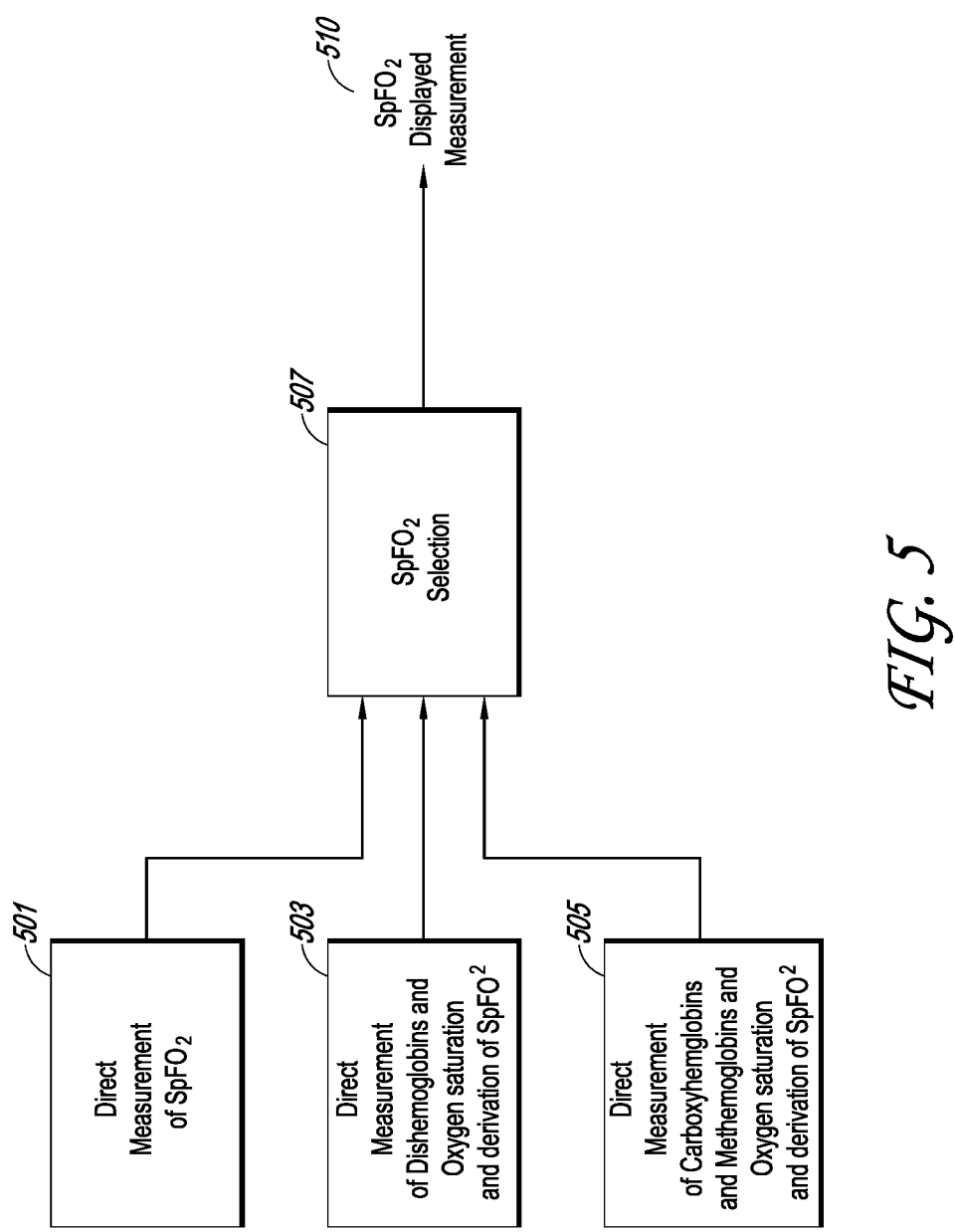
FIG. 5 illustrates a fractional oxygen saturation determination system for determining fraction oxygen saturation from a plurality of different fraction oxygen saturation measurements.

FIG. 5 illustrates an embodiment of a system that calculates a plurality of fractional oxygen saturation measurements and then determines which of the measurements to use in a final measurement. As illustrated in FIG. 5, a direct measurement of fractional oxygen saturation is determined at module 501. At module 503, a derived measurement fractional oxygen saturation is determined from a measurement of oxygen saturation and a direct dishemoglobin measurement. At module 505, a derived measurement fractional oxygen saturation is determined from a measurement of carboxyhemoglobin and methemoglobin measurements as described above. SpFO$_2$ determination module 507 then determines a final fraction oxygen saturation measurement 510. In an embodiment, the determination module looks at a signal confidence value to determine which measurement to use. If the signal confidence is low, the determination module 507 will use one or both of the output of modules 503 and 505. If the signal confidence is high, the determination module 507 will use the output of module 501. In an embodiment, the determination module 507 is configured to use an average or weighted average of all three measurements. In an embodiment, only two measurements are used. In an embodiment, more than three different determinations of fraction oxygen saturation are used and the determination modules 507 then determines an appropriate output.

Although the foregoing has been described in terms of certain specific embodiments, other embodiments will be apparent to those of ordinary skill in the art from the disclosure herein. Moreover, the described embodiments have been presented by way of example only, and are not intended to limit the scope of the disclosure. Indeed, the novel methods and systems described herein may be embodied in a variety of other forms without departing from the spirit thereof. Accordingly, other combinations, omissions, substitutions, and modifications will be apparent to the skilled artisan in view of the disclosure herein. Thus, the present disclosure is not limited by the preferred embodiments, but is defined by reference to the appended claims. The accompanying claims and their equivalents are intended to cover forms or modifications as would fall within the scope and spirit of the disclosure.

The methods, steps, processes, calculations, computations or the like ("methods") provided herein are simplified examples that are generally performed by advanced processing devices, including complex signal processors, sensitive analog and digital signal preprocessing boards, optical/optoelectronic componentry, display drivers and devices, or similar electronic devices. An artisan will recognize from the disclosure herein that the various methods often must be performed at speeds that, as a practical matter, could never be performed entirely in a human mind. Rather, for many calculations providing real time or near real time solutions, outputs, measurements, criteria, estimates, display indicia, or the like, many of the foregoing processing devices perform tens to billions or more calculations per second. In addition, such processing devices may process electrical signals, infrared signals, wireless signals, or other electromagnetic wave signals that are incomprehensible to a human mind in their raw form and at the speeds communicated.

What is claimed is:

1. A patient monitoring apparatus comprising:
   a housing;
   a memory device configured to store a signal generated by a noninvasive physiological sensor that monitors a patient, the signal being responsive to a physiological condition of the patient; and
   one or more hardware processors in communication with the memory device, the one or more hardware processors being configured to:
   determine a carboxyhemoglobin measurement from the signal,
   determine whether the patient has a first methemoglobin condition or a second methemoglobin condition,
   responsive to determining that the patient has the first methemoglobin condition,
   reduce the carboxyhemoglobin measurement to obtain a reduced carboxyhemoglobin measurement, and output for presentation a first parameter measurement responsive to the reduced carboxyhemoglobin measurement, and responsive to determining that the patient has the second methemoglobin condition, output for presentation a second parameter measurement.

2. The patient monitoring apparatus of claim 1, wherein the one or more hardware processors is configured to, responsive to determining that the patient has the second methemoglobin condition, not reduce the carboxyhemoglobin measurement, and the second parameter measurement is responsive to carboxyhemoglobin measurement.

3. The patient monitoring apparatus of claim 1, wherein the second parameter measurement is responsive to a predetermined carboxyhemoglobin value.

4. The patient monitoring apparatus of claim 1, wherein the one or more hardware processors is configured to reduce the carboxyhemoglobin measurement by an amount that depends on a magnitude of the carboxyhemoglobin measurement.

5. The patient monitoring apparatus of claim 1, wherein the one or more hardware processors is configured to determine whether the carboxyhemoglobin measurement reflects a changed condition for the patient or an anomalous measurement.

6. The patient monitoring apparatus of claim 1, wherein the one or more hardware processors is configured to determine whether the patient has the first methemoglobin condition or the second methemoglobin condition from the signal.

7. The patient monitoring apparatus of claim 6, wherein the one or more hardware processors is configured to use a multivariate classifier to determine whether the patient has the first methemoglobin condition or the second methemoglobin condition.

8. The patient monitoring apparatus of claim 6, wherein the one or more hardware processors is configured to:
determine a methemoglobin measurement from the signal, and
determine whether the patient has the first methemoglobin condition or the second methemoglobin condition from a comparison of the methemoglobin measurement and a methemoglobin threshold.

9. The patient monitoring apparatus of claim 1, wherein the one or more hardware processors is configured to determine the first parameter measurement from the reduced carboxyhemoglobin measurement, the first parameter measurement being indicative of a fractional oxygen saturation.

10. The patient monitoring apparatus of claim 1, further comprising a display configured to present the first parameter measurement.

11. The patient monitoring apparatus of claim 1, further comprising the noninvasive physiological sensor, the noninvasive physiological sensor comprising an optical sensor configured to generate the signal.

12. The patient monitoring apparatus of claim 1, wherein the signal is representative of light that is detected after attenuation by tissue of the patient.

13. The patient monitoring apparatus of claim 1, wherein the signal is representative of light of three or more wavelengths that is detected after attenuation by tissue of the patient, and the one or more hardware processors is configured to determine the carboxyhemoglobin measurement from the light of three or more wavelengths that is detected after attenuation.

14. The patient monitoring apparatus of claim 1, wherein the one or more hardware processors is configured to output the second parameter measurement for presentation in place of the first parameter measurement on a display.

15. A method of patient monitoring, the method comprising:
generating, by a noninvasive physiological sensor monitoring a patient, a signal responsive to a physiological condition of the patient;
determining, by one or more hardware processors, a first carboxyhemoglobin measurement from the signal;
determining, by the one or more hardware processors, that the patient has a first methemoglobin condition at a first time;
in response to determining that the patient has the first methemoglobin condition at the first time,
reducing, by the one or more hardware processors, the first carboxyhemoglobin measurement to obtain a reduced carboxyhemoglobin measurement,
determining, by the one or more hardware processors, a first parameter measurement from the reduced carboxyhemoglobin measurement, and
presenting, by a display, the first parameter measurement;
determining, by the one or more hardware processors, a second carboxyhemoglobin measurement from the signal;
determining, by the one or more hardware processors, that the patient has a second methemoglobin condition at a second time, the second methemoglobin condition being different from the first methemoglobin condition; and
in response to determining that the patient has the second methemoglobin condition at the second time,
determining, by the one or more hardware processors, a second parameter measurement, and
presenting, by the display, the second parameter measurement.

16. The method of claim 15, further comprising:
in response to determining that the patient has the second methemoglobin condition at the second time,
not reducing, by the one or more hardware processors, the second carboxyhemoglobin measurement, or
using, by the one or more hardware processors, a predetermined carboxyhemoglobin value in place of the second carboxyhemoglobin measurement.

17. The method of claim 15, further comprising determining, by the one or more hardware processors, whether the patient has the first methemoglobin condition or the second methemoglobin condition from the signal.

18. The method of claim 15, wherein the first parameter measurement and the second parameter measurement are fractional oxygen saturation measurements.

19. The method of claim 15, wherein the signal is representative of light of three or more wavelengths that is detected after attenuation by tissue of the patient, and the first carboxyhemoglobin measurement and the second carboxyhemoglobin measurement are determined from the light of three or more wavelengths that is detected after attenuation.

* * * * *